United States Patent [19]

Hill

[11] Patent Number: 4,877,322

[45] Date of Patent: Oct. 31, 1989

[54] METHOD AND APPARATUS FOR MEASURING BLOOD OXYGEN LEVELS IN SELECTED AREAS OF THE EYE FUNDUS

[75] Inventor: Robert V. Hill, Portland, Oreg.

[73] Assignee: Eyedentify, Inc., Portland, Oreg.

[21] Appl. No.: 235,692

[22] Filed: Aug. 22, 1988

Related U.S. Application Data

[63] Continuation of Ser. No. 44,800, Apr. 30, 1987, abandoned.

[51] Int. Cl.$^4$ ............................ A61B 3/10; A61B 5/00
[52] U.S. Cl. ...................................... 351/221; 128/633
[58] Field of Search ........................ 351/221, 205, 206; 128/133, 134, 633, 666; 356/28.5, 41

[56] References Cited

U.S. PATENT DOCUMENTS

4,305,398 12/1981 Sawa ............................. 128/633
4,485,820 12/1984 Flower ........................... 356/41

OTHER PUBLICATIONS

Laing, R. A. et al, I.E.E.E. Trans. on Biomed. Engng., vol.-BME 22, No. 3, pp. 183-195, May 1975.

Primary Examiner—P. M. Dzierzynski
Attorney, Agent, or Firm—Eugene D. Farley

[57] ABSTRACT

This invention provides for the measurement of relative oxygen saturation of the choriodal blood of the fundus of the eye of a subject by directing into the eye a source beam of light including incandescent, red and infrared light, the combined beam penetrating the choroid and impinging on the sclera of the eye, the beam then being reflected back out of the eye as a collimated beam of light. The collimated beam of light is directed to a dichroic beam splitter where the red and infrared light are separated from the beam and are subject to the measurement of their respective intensities. The measured intensities of the red and infrared light components of the collimated beam reflected from the eye are compared with the measured intensities of the red and infrared light components of the separated portion of the source beam of light to determine the ratio of oxyhemoglobin to reduced hemoglobin.

9 Claims, 4 Drawing Sheets

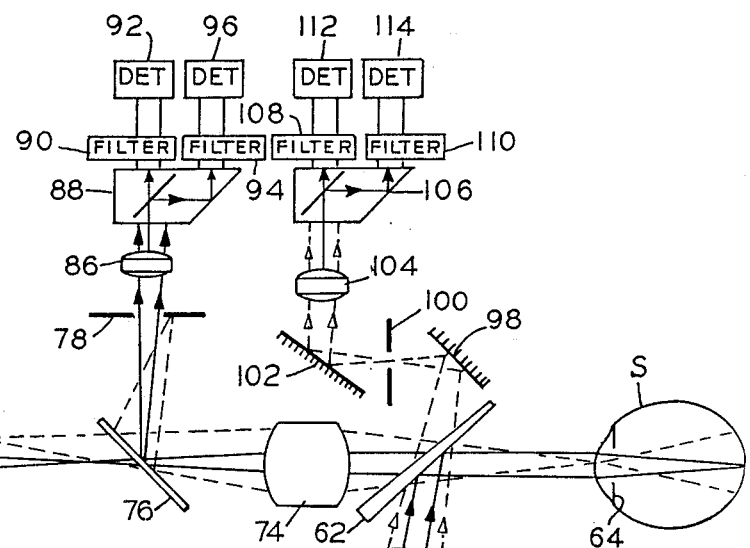
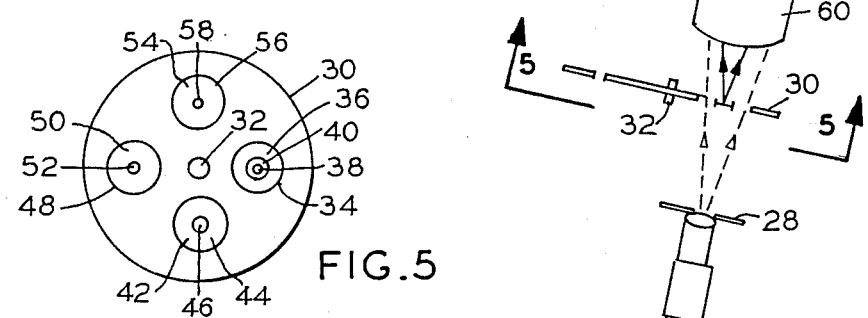
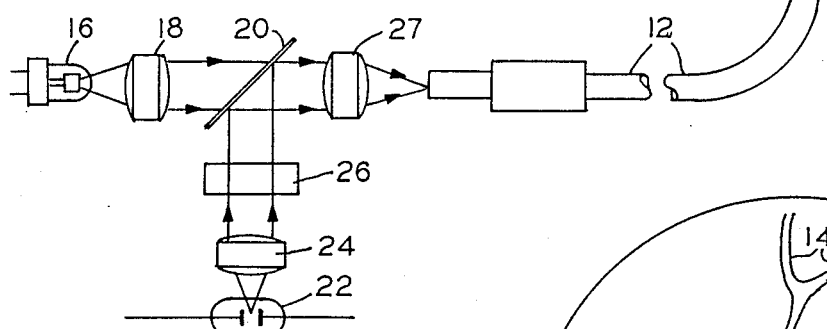
FIG. 4
FIG. 5
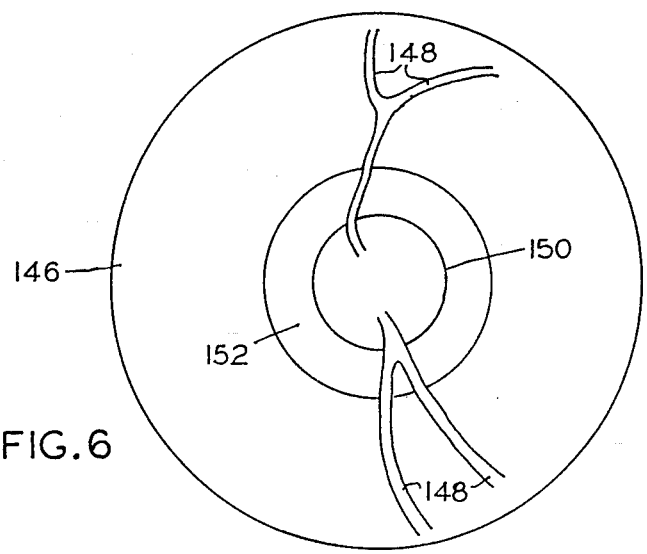
FIG. 6

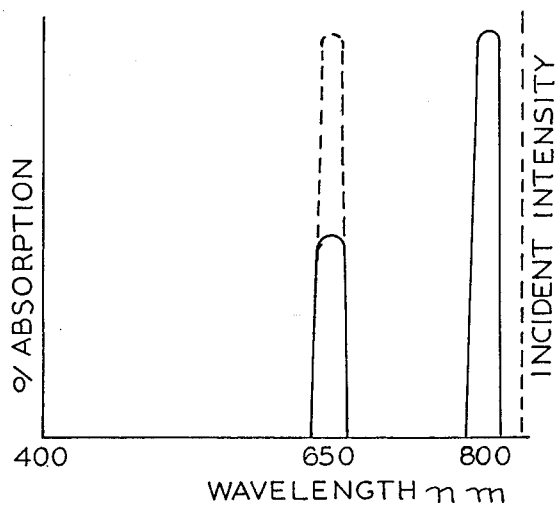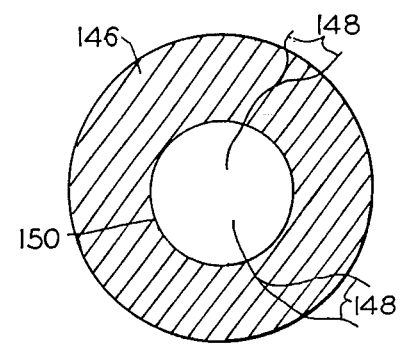
FIG. 8
FIG. 8a
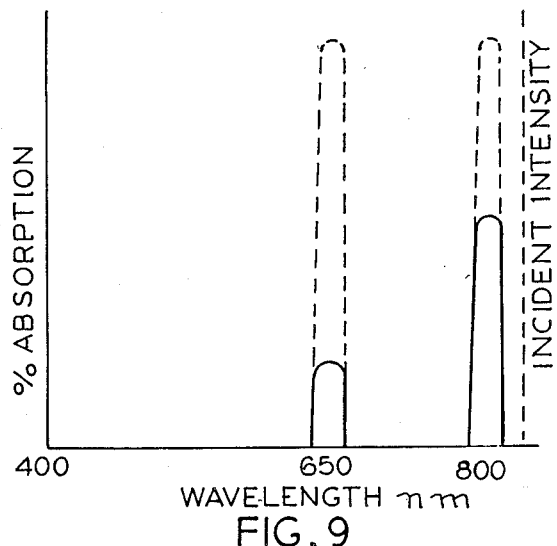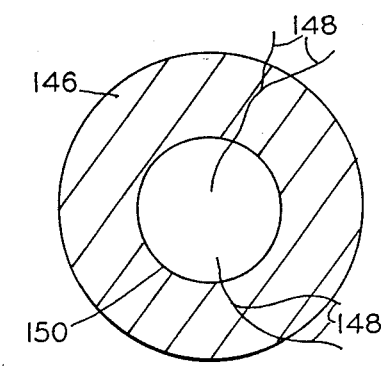
FIG. 9
FIG. 9a
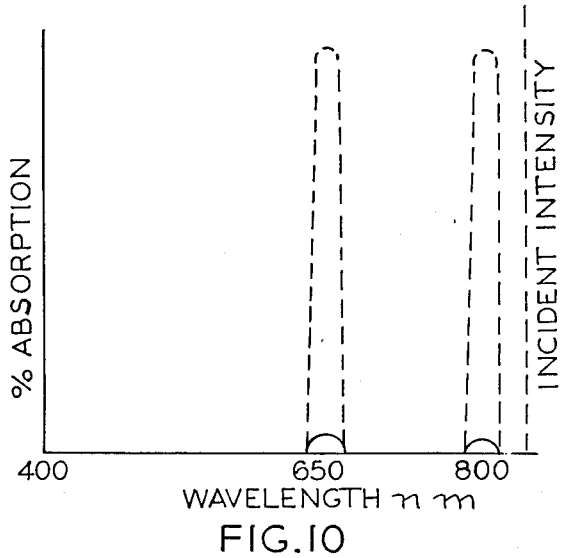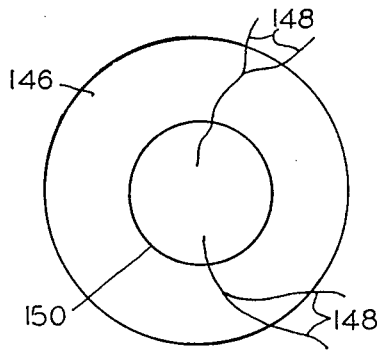
FIG. 10
FIG. 10a

4,877,322

METHOD AND APPARATUS FOR MEASURING BLOOD OXYGEN LEVELS IN SELECTED AREAS OF THE EYE FUNDUS

This application is a continuation of application Ser. No. 044,800, filed Apr. 30, 1987, now abandoned.

BACKGROUND OF THE INVENTION

This invention relates to the measurement of relative oxygen saturation of choroidal blood of the eye fundus, and more particularly to such measurements in specifically selected areas of the eyegrounds.

Recent evidence, obtained by means of special infrared photographic techniques, has demonstrated an important distinctiveness of the blood capillary distribution of the two most critical areas of the posterior pole fundus eyegrounds. These are the peripapillary area adjacent to, and surrounding the optic nerve head and the macular area which is the center of vision for form and color. These areas are critically important to vision because they are involved in the two leading causes of blindness; namely, glaucoma and macular degeneration. The recent infrared photographic evidence has shown that the capillary blood (choriocapillaris) in these two areas diminishes and ultimately disappears with progression of the diseases of glaucoma and macular degeneration. Fortunately, these two causes of blindness rarely occur together in the same individual. However, early diagnostics could improve the prognoses of these diseases by reason of the consequent earlier and therefore more effective treatment.

A successful method and instrumentation for measuring the relative oxygen saturation of the choroidal blood of the eye fundus is disclosed by Laing et al in IEEE TRANSACTIONS ON BIOMEDICAL ENGINEERING, Volume BME-22, No. 3, May 1975, Pages 183–195, entitled THE CHOROIDAL EYE OXIMETER: AN INSTRUMENT FOR MEASURING OXYGEN SATURATION OF CHOROIDAL BLOOD IN VIVO. In this disclosure, only fields of view of the eyegrounds which were larger than 10° were used. However, such large spectral sampling areas are too large to separate the two critically important areas; namely, the macula and peripapillary. Moreover, the instrumentation is so large, heavy and non-portable that its use is limited. Moreover, the large angle of the field of view renders the method and instrumentation inefficient since it is essential to be able to study accurately either the optic disc or the macula without overlapping by the other.

SUMMARY OF THE INVENTION

In its basic concept, this invention provides for the measurement of relative oxygen saturation of choroidal blood in specifically selected areas of the eyegrounds by utilizing a selectable field stop of dichroic masking material of certain aperture geometry which blocks light of a specific range of wavelength and allows the remaining wavelength of light to form an image of the selected aperture on a specific area of the eyeground.

It is by virtue of the foregoing basic concept that the principal objective of this invention is achieved; namely, the provision of method and apparatus which overcome the aforementioned limitations and disadvantages of the prior art.

Another important objective of this invention is the provision of method and apparatus of the class described which is capable of optically viewing a specific area of the fundus eyegrounds, such as the optic disc and macula, each independently of the other.

Still another objective of this invention is to provide method and apparatus of the class described which enables the spectro-optically taking of an oximetric sample of a specific area of the fundus eyegrounds.

A further important objective of this invention is the provision of apparatus of the class described which is readily portable and usable in the hand-held manner of a conventional ophthalmoscope.

A still further objective of this invention is the provision of apparatus of the class described which is of relatively simplified construction for economical manufacture and maintenance and which is reproducibly precise in its mode of operation.

The foregoing and other objects and advantages of this invention will appear from the following detailed description, taken in connection with the accompanying drawings of a preferred embodiment.

BRIEF DESCRIPTION OF THE DRAWINGS

FIG. 4 is a schematic diagram of the optical system of the apparatus of this invention.

FIG. 5 is a front elevation of the field stop component of FIG. 4 as viewed in the direction of the arrows 5—5 in FIG. 4.

FIG. 6 is a schematic front view of an eye showing the operational mode of the apparatus of this invention.

FIG. 8 is a graph of peripapillary oximetric and plethysmographic ratio changes in a normal eye, and FIG. 8a is a schematic front view of the capillary bed of such normal eye.

FIG. 9 is a graph similar to FIG. 8 but showing the ratio changes for an eye exhibiting moderate glaucoma, and FIG. 9a is a schematic front view of the capillary bed of such eye with moderate glaucoma.

FIG. 10 is a graph similar to FIGS. 8 and 9 but showing the ratio changes in an eye exhibiting terminal glaucoma, and FIG. 10a is a schematic front view of the capillary bed of such eye exhibiting terminal glaucoma.

DESCRIPTION OF THE PREFERRED EMBODIMENT

Figure 1:
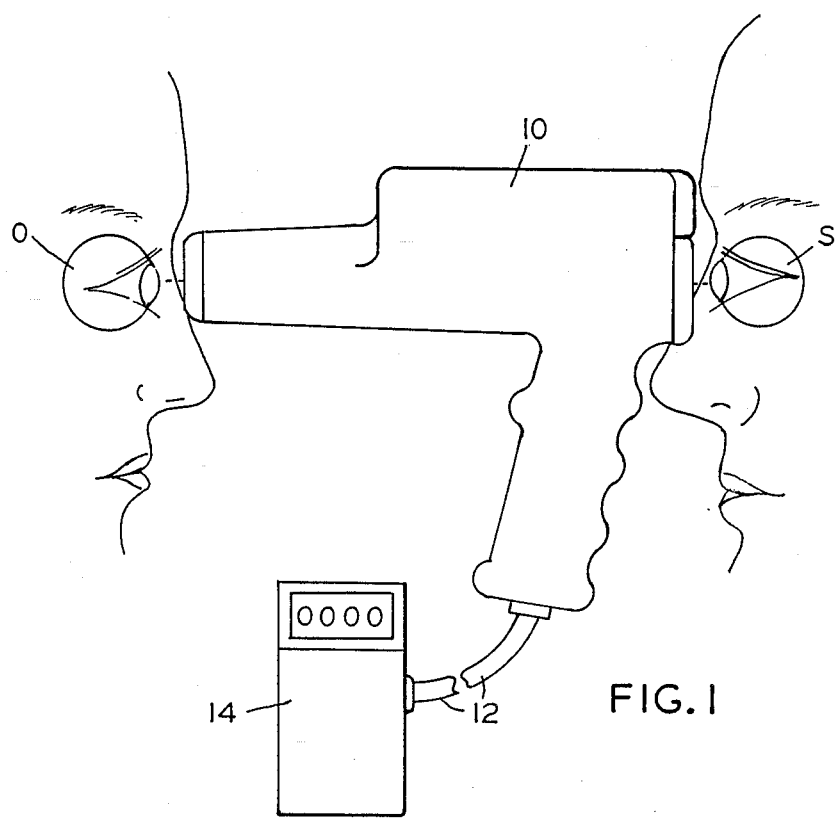
FIG. 1 is a fragmentary, foreshortened side elevation showing the operational mode of the apparatus of the invention.

FIG. 1 of the drawings illustrates a conventional opthalmoscope body 10 containing the optical system and connected through fiber optic cable 12 to the control circuitry in housing 14. The opthalmoscope is shown in position for the eye 0 of a physician or other observer to view the interior of the eye S of a patient or other subject.

The optical system illustrated in FIG. 4 is intended to show how a conventional opthalmoscope is modified to include, in addition to its normal function of viewing the interior back of the eye, means for spectroscopically determining the blood oxygen saturation levels of selected areas of the eyegrounds. For both ophthalmoscopy and oximetric spectroscopy, two separate light sources are utilized. In the embodiment illustrated, incandescent light from a light bulb source 16 is collimated by a lens 18 and the collimated beam passes through a dichroic beam splitter 20.

Simultaneously, a high intensity xenon flash source 22 produces a light beam which is collimated by a lens 24. The collimated beam is passed through a dual filter 26 which allows the selected bandwidths of red light (approximately 620 nm to 780 nm) and infrared radiation (about 840 nm to 930 nm), to pass to the beam splitter 20 from whence it reflects from the back surface thereof and combines with the beam from the incandescent light source 16.

The combined beam passes through lens 27, is focused onto the fiber optic cable 12 and then through pinhole 28 to a selected field stop mounted on a rotary support 30 which in turn is mounted on a shaft 32 for adjustable axial rotation. The field stop assembly is illustrated in greater detail in FIG. 5. In the embodiment illustrated, the rotary support 30 mounts four discrete field stops. The field stop 34 shown in operative position in FIG. 4 and located at the 3 o'clock position of the rotary support in FIG. 5 is provided with an outer annular portion 36 of dichroic material and a central spot area 38 of the same dichroic material, separated from the outer annular area by a clear annular area 40. The field stop 42 shown in the 6 o'clock position in FIG. 5 includes an annular area 44 of dichroic material surrounding a central clear area 46 of a selected size. The field stop 48 shown in the 9 o'clock position has the same outer annular area 50 of dichroic material as the 6 o'clock position but provided with a central clear area 52 of smaller size. The field stop 54 shown in the 12 o'clock position has the same annular area 56 of dichroic material and a still smaller central clear area 58 than the 9 o'clock position.

The combined beam passes through the selected field stop, thence through the converging lenses 60 to the neutral beam splitter 62. The combined beam reflects from the back surface of the beam splitter 62 and comes to a focus at the pupillary plane 64 inside the eye S of the subject. This plane is conjugate to the pinhole source 28 and diffusely illuminates the interior of the eye by the diverging cone of the source beam, as indicated by the broken lines in FIG. 4 extending between the pinhole (28) and the pupillary plane. Also, the aperture of the selected field stop, for example field stop 34 illustrated in FIG. 5, is positioned at the conjugate focus of the retina of the eye (S), as indicated by the solid lines of FIG. 4 extending between the field stop support (30) and the retina of the eye (S).

Figure 2:
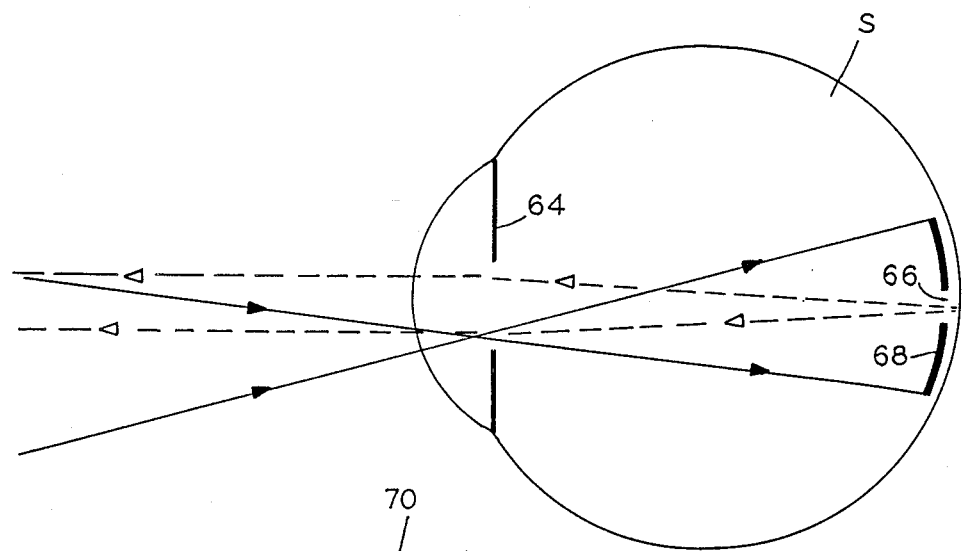
FIG. 2 is a schematic side view of the interior of an eye showing the configuration of light rays associated with the operation of the apparatus of this invention.
Figure 3:
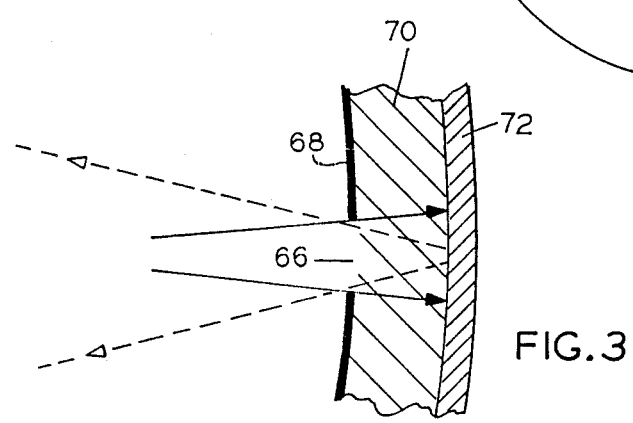
FIG. 3 is a fragmentary sectional view, on an enlarged scale, of the portion of the eye scanned in FIG. 2.

This diffuse cone of light in the back of the eye then enters the eyeground tissue through the hole 66 of the graticule bar mask shadow 68 (FIG. 3). After entering the hole in the mask the source beam, which contains the low intensity fundus viewing light and the pulsed higher intensity light from the xenon source, penetrates the blood-containing choroid layer 70 and impinges on the specular reflecting surface of the back wall or sclera 72 of the eye. The beam returns through the choroid and through the hole 66 in the mask 68 to form a reflecting cone of light. This cone of light is reflected back toward the beam splitter 62, but will now have been auto-collimated by the eye. As illustrated in FIG. 2 of the drawings, this collimated beam is spaced laterally from the focused source beam at the pupillary plane 64. This results in a real-time, reflection-free view of the eyegrounds by both the operator 0 and the spectroscopic detectors described hereinafter. This collimated beam is transmitted by the beam splitter 62 to the converging lenses 74 from whence they come to a focus at the dichroic beam splitter 76.

The beam splitter 76 reflects all of the light of 620 nm wavelength and longer to aperture stop 78, while transmitting all of the light of 620 nm wavelength and shorter to aperture stop 80, thence through converging lens 82 to collimating lens 84. Between the lenses 82 and 84 an upright image of the eyegrounds of the eye is formed, and this image is viewed by the eye 0 of the physician or other observer through the collimating lens 84.

The beam from the aperture stop 78 is collimated by collimating lens 86 and is then split by the dichroic beam splitter 88. The 620 nm to 780 nm wavelengths pass through it to interference filter 90 where all but the selected wavelengths, centered at 700 nm, are rejected. The beam then enters photodetector 92.

The wavelengths of 840 nm and longer are reflected from the dichroic beam splitter 88 to an internal reflecting surface of the solid cube containing the dichroic beam splitter. The reflected beam from the internal surface passes through the interference filter 94 which passes wavelengths of 840 nm and longer on to the photodetector 96.

The image of the light source at pinhole 28 has three conjugates, one at the pupillary plane 64 of the eye and one each at the aperture stops 78 and 80. This arrangement of illuminating the eye through a different part of the pupil of the eye than that part which reflects the auto-collimated light of the eyeground image, allows an effective separation of the corneal reflection image of the source from the eyeground image, as seen at the aperture stops.

Additional opto-electronics is needed for the purpose of calibrating each xenon flash from source 22, since their spectral content and intensity may vary slightly in successive flashes. One half of the combined beam which reaches the beam splitter 62 is reflected into the eye S while the other half is transmitted to a mirror 98 from whence it is reflected through the field stop 100 to the mirror 102. The beam is reflected from the mirror 102 to the collimating lens 104 from whence the collimated light impinges on the dichroic beam splitter 106. Here the red light is transmitted to the interference filter 108 and the infrared light reflects to the interference filter 110. The photodetector 112 receives the red light from the filter 108 and the photodetector 114 receives the infrared radiation from the filter 110. The interference filters 108 and 110 and the detectors 112 and 114 are duplicates of the filters 90 and 94 and detectors 92 and 96 and they serve the same basic purpose of measuring the intensities of the red and infrared light. The important difference is that the detectors 112 and 114 receive the light before it enters the eye S, whereas the detectors 92 and 96 receive the light after it has passed through the eyeground sample area within the eye. Accordingly, variances in light source spectral content, as well as intensity, can be effectively cancelled. This is accomplished by electronic comparison of the light measured by the four detectors.

Figure 7:
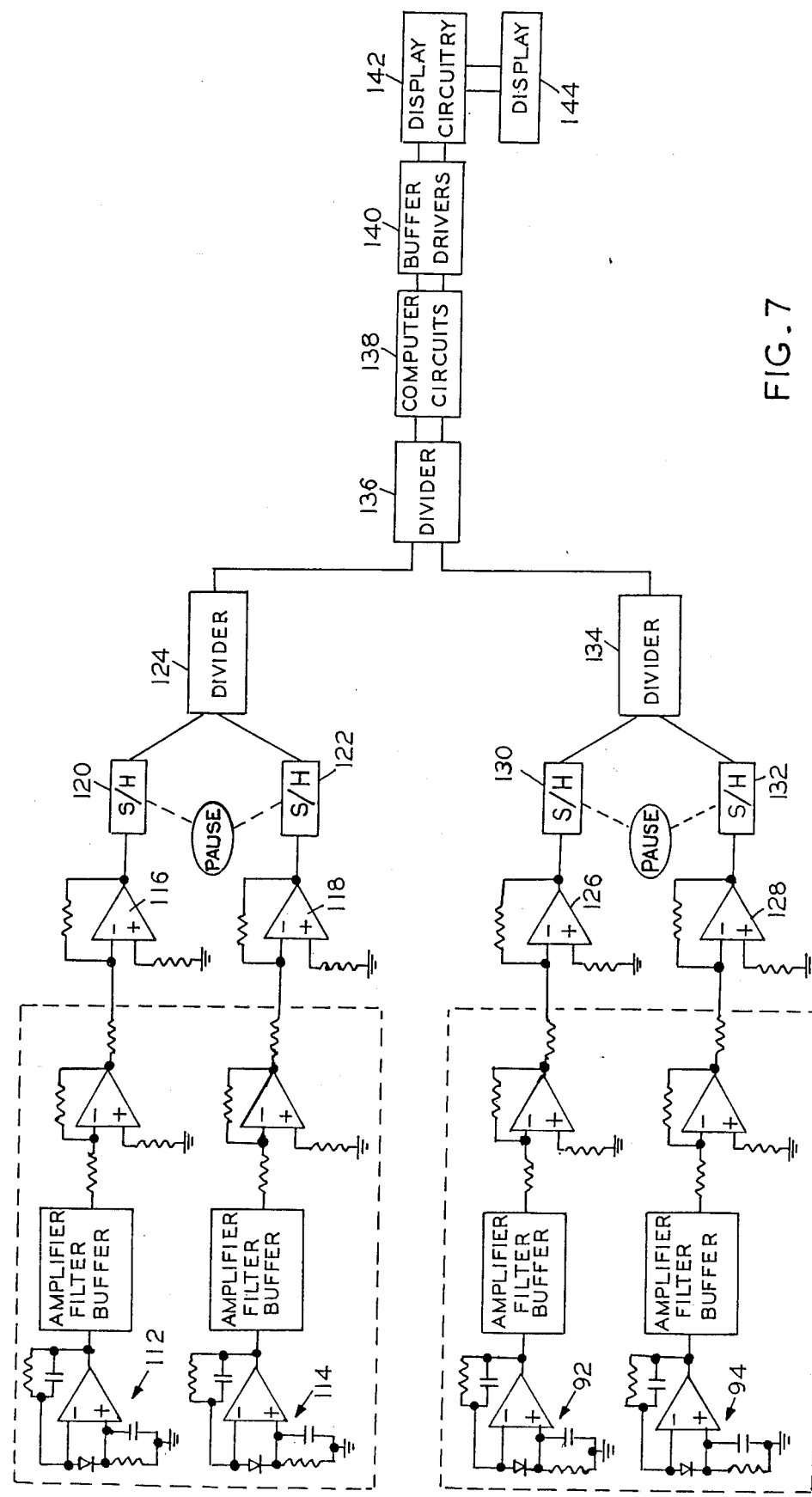
FIG. 7 is a schematic electrical diagram of control circuitry for the apparatus of this invention.

Referring to FIG. 7 of the drawings, the light source detection system utilizes filters 108 and 110 and the photodetectors 112 and 114 to separate the two bands of wavelengths of red and infrared light, while the oximeter detection system utlizes filters 90 and 94 and the photodetectors 92 and 96 to separate the same two bands. The photodetector output of each separated band passes through operational amplifiers for amplification, thence through electronic low pass filtering and buffering to a current mode before the next stage. The basic difference between the light source detection system and the oximeter detection system is the amount of gain amplification to each band of light so the respective output will not saturate the following stages or subsequent devices.

The currents resulting from the red and infrared detectors 112 and 114 bands of light are passed to individual current-to-voltage buffer converters 116 and 118, each with unity gain. The outputs of these converters pass to associated sample and hold devices 120 and 122 and are held under a monostable condition (pulse) synchronized by the xenon flash tube trigger. These outputs become the inputs to the divider 124 such that its output will be ten times the division of the inputs. This completes the phase which is the ratio of the light source detection system.

The currents resulting from the red and infrared detectors 92 and 94 similarly pass to current-to-voltage buffer converters 126 and 128, each with unity gain. The outputs of these converters pass to associated sample and hold devices 130 and 132 and are held under a monostable condition (pulse) synchronized by the xenon flash tube trigger. They provide the inputs to the divider 134 such that the output will be ten times the division of the inputs. This completes the phase which determines the ratio of the oximeter detection system.

The next phase is the determination of the ratio between the two different quotients, at 124 and 134 and this is accomplished by passing the outputs of the dividers 124 and 134 to the next divider 136. The output of this divider is passed through computational circuitry 138 for scaling factors, offsets, etc. The output from this computational circuitry is passed through buffer drivers 140, display circuitry 142 and finally to the display 144 where the numerical values of the ratio of oxyhemoglobin to reduced hemoglobin are presented.

An example of the potential usefulness of the invention for the diagnosis and follow-up in the eye disease, glaucoma, is shown in FIGS. 6 and 8-10. Infrared photographs have revealed that the blood supply 152 within the eyeground area 146, which is immediately adjacent to and surrounds the optic nerve head (peripapillary) gradually diminishes and completely disappears as glaucoma progresses to its end stage, where total blindness ensues. Retinal blood vessels 148 and optic disc margin 150 remain relatively unchanged, for they play no role in the progress of the disease.

The schematic graphs of FIGS. 8, 9 and 10 and the associated eyeground peripapillary area that they represent and which are shown in related FIGS. 8a, 9a, and 10a, reveal two important and related phenomena within the peripapillary area, with respect to progression of the disease; namely, a lowering of the oxyhemoglobin to reduced hemoglobin ratio, illustrated in FIGS. 8a, 9a and 10a by the diminished cross hatchings in the areas 152, as well as a loss of blood volume. Blood volume measurements are also sometimes called plethysmography, and this can also be performed in the peripapillary eyeground area with the apparatus of this invention simply by shutting off the red light and allowing only the infrared light through. The infrared light is absorbed equally by all of the blood hemoglobin, and this is measured before and after passing into and out of the eye 0.

A representation of the projected graticule onto the peripapillary eyeground tissue is shown in FIG. 6. As seen by the observer, the entire field of view of the eyeground 146 will have a slightly bluish-green tint, except for the annulus 152, because the red and infrared light from the source is blocked everywhere else at the field stop 30. The optic disc, inside the disc margin 150 will have the bluish-green tint, but the retinal vessels 148 will have their normal reddish color within the annulus graticule.

It will be understood by those skilled in the art that various changes may be made in the structural details described hereinbefore. For example, the combined source beam for the reference detectors can be acquired at any convenient place between the dichroic beam splitter 20 and a neutral beam splitter 62. Further, the system providing the combined beam source may be replaced by any comparable system which combines the opthalmoscopic view light with the signal source light. For example, light emitting diodes or laser diodes may be used instead of the xenon arc illustrated to provide the red and infrared signal sources. These and other changes may be made, as desired, without departing from the spirit of this invention and the scope of the appended claims. Further, various selections of bandwidths of red and infrared light may be chosen, such that optionization of signal is obtained. For example, some wavelengths may be more reflective than others for a given eyeground, and these wavelengths could be omitted in the signal light source.

I claim:

1. The method of measuring the relative oxygen saturation of the choroidal blood of only a specifically selected area of the fundus of the eye of a subject, to the exclusion of any unselected area, comprising:

(a) providing a light source including incandescent light, pulsed red light of 620–780 nm wavelength and pulsed infrared light of 840–930 nm wavelength, (b) passing said light source through a field stop of dichroic masking material selected to block the passage therethrough of said pulsed red and infrared wavelengths and having an aperture positioned at the conjugate focus of the eye retina, the aperture being of predetermined geometry for outlining with sharply defined borders only a specifically selected area of the fundus, (c) focusing the light source at the pupillary plane of the subject's eye and passing said light into the subject's eye to diffusely illuminate an area of the fundus and to form within said diffusely illuminated area a sharply defined image of said aperture on the fundus for positioning said aperture on the selected area of the fundus to the exclusion of any unselected area, the source and aperture light being reflected back out of the eye as a collimated beam of light, (d) passing the collimated beam to an observer's eye for viewing of the eyegrounds of the eye of the subject, (e) measuring the intensity of pulsed red light from the light source, (f) measuring the intensity of pulsed infrared light from the light source, (g) measuring the intensity of the pulsed red light from the reflected collimated beam, (h) measuring the intensity of the pulsed infrared light from the reflected collimated beam,
(i) comparing the measured intensities of the pulsed red light of the light source and the pulsed red light of the collimated beam reflected from the eye, and
(j) comparing the measured intensities of the pulsed infrared light of the light source and the pulsed infrared light of the collimated beam reflected from the eye.

2. The method of measuring the relative oxygen saturation of the choroidal blood of only a specifically selected area of the fundus of the eye of a subject, comprising:
   (a) providing a light source including incandescent light, pulsed red light of 620–780 nm wavelength and pulsed infrared light of 840–930 nm wavelength,
   (b) passing said light source through a field stop of dichroic masking material selected to block the passage therethrough of said pulsed red and infrared wavelengths and having an aperature positioned at the conjugate focus of the eye retina, the aperture being of predetermined geometry for outlining with sharply defined borders only a specifically selected area of the fundus,
   (c) separating pulsed red and infrared light from the light source,
   (d) measuring the intensity of pulsed red light separated from the light source,
   (e) measuring the intensity of pulsed infrared light separated from the light source,
   (f) focusing the light source at the pupillary plane of the subject's eye and passing said light into the subject's eye to diffusely illuminate an area of the fundus and to form within said diffusely illuminated area a sharply defined image of said aperture on the fundus for positioning said aperture on the selected area of the fundus to the exclusion of any unselected area, the source and aperture light being reflected back out of the eye as a collimated beam of light,
   (g) separating pulsed red and infrared light from the reflected collimated beam,
   (h) passing the reflected collimated beam to an observer's eye for viewing of the eyegrounds of the eye of the subject,
   (i) measuring the intensity of the pulsed red light separated from the reflected collimated beam,
   (j) measuring the intensity of the pulsed infrared light separated from the reflected collimated beam,
   (k) comparing the measured intensities of the pulsed red light of the light source and the pulsed red light of the collimated beam reflected from the eye, and
   (l) comparing the measured intensities of the pulsed infrared light of the light source and the pulsed infrared light of the collimated beam reflected from the eye.

3. The method of claim 2 wherein the light source is provided by combining incandescent light from a source thereof with red and infrared light from a pulsed source thereof.

4. The method of claim 2 wherein the separation of the pulsed red and infrared light from the light source and reflected collimated beams is achieved by directing the beams to dichroic beam splitters.

5. The method of claim 2 wherein the separation of the light source for passing one portion to the eye and another portion for separation of the red and infrared light therefrom is achieved by directing the light source to a neutral splitter.

6. Apparatus for measuring the relative oxygen saturation of the choroidal blood of only a specifically selected area of the fundus of the eye of a subject, comprising:
   (a) a light source including incandescent light, pulsed red light of 620–780 wavelength and pulsed infrared light of 840–930 nm wavelength,
   (b) field stop means of dichroic masking material selected to block the passage therethrough of said pulsed red and infrared wavelengths and having an aperture positioned at the conjugate focus of the eye retina, the aperture being of predetermined geometry for outlining with sharply defined borders only a specifically selected area of the fundus,
   (c) beam splitter means arranged to receive the light source from said field stop means for separating the light source into one portion directed to be focused at the pupillary plane of the subject's eye and to enter the subject's eye to diffusely illuminate an area of the fundus and to form within said diffusely illuminated area a sharply defined image of said aperture on the fundus for positioning said aperture on the selected area of the fundus to the exclusion of any unselected area, the source and aperture light being reflected back out of the eye as a collimated beam of light, and a second portion directed toward light intensity measuring means,
   (d) light intensity measuring means arranged to receive the pulsed red light from said second portion of the light source for measuring the intensity of said pulsed red light,
   (e) light intensity measuring means arranged to receive the pulsed infrared light from said second portion of the light source for measuring the intensity of said pulsed infrared light,
   (f) beam splitter means arranged to receive the reflected collimated beam from the eye for separating the pulsed red and infrared light from the reflected collimated beam,
   (g) lens means arranged to receive the reflected collimated beam and direct it to an observer's eye for viewing the eyegrounds of the subject,
   (h) light intensity measuring means arranged to receive the pulsed red light from said reflected collimated beam for measuring the intensity of said pulsed red light,
   (i) light intensity measuring means arranged to receive the pulsed infrared light from said reflected collimated beam for measuring the intensity of said pulsed infrared light,
   (j) light intensity comparing means associated with the measuring means for comparing the measured intensities of the pulsed red light of the separated light source and the pulsed red light of the collimated beam reflected from the subject's eye, and
   (k) light intensity comparing means associated with the measuring means for comparing the measured intensities of the pulsed infrared light of the light source and the pulsed infrared light of the collimated beam reflected from the subject's eye.

7. The apparatus of claim 6 wherein the light source includes an incandescent light source and a pulsed source of red and infrared light, and a beam splitter arranged to intercept and combine said light sources.

8. The apparatus of claim 6 wherein the beam splitter means for separating the red and infrared light from the light source and from the reflected collimated are dichroic beam splitters.

9. The apparatus of claim 6 wherein the beam splitter means for separating the light source beam into said one and second portions is a neutral splitter.

* * * * *